US009885089B2

(12) United States Patent
Ley et al.

(10) Patent No.: US 9,885,089 B2
(45) Date of Patent: Feb. 6, 2018

(54) FLAGELLUM AND ANTI-FLAGELLUM ANTIBODY LEVELS IN SAMPLES AS A DIAGNOSTIC BIOMARKER AND THERAPEUTIC TARGET FOR METABOLIC SYNDROME

(71) Applicant: CORNELL UNIVERSITY, Ithaca, NY (US)

(72) Inventors: Ruth E. Ley, Ithaca, NY (US); Tyler Cullender, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/383,188

(22) PCT Filed: Mar. 5, 2013

(86) PCT No.: PCT/US2013/029050
§ 371 (c)(1),
(2) Date: Sep. 5, 2014

(87) PCT Pub. No.: WO2013/134224
PCT Pub. Date: Sep. 12, 2013

(65) Prior Publication Data
US 2015/0050293 A1   Feb. 19, 2015

Related U.S. Application Data

(60) Provisional application No. 61/606,522, filed on Mar. 5, 2012.

(51) Int. Cl.
| | |
|---|---|
| *C12Q 1/68* | (2006.01) |
| *G01N 33/68* | (2006.01) |
| *A61K 49/00* | (2006.01) |
| *A61K 39/40* | (2006.01) |
| *A61K 45/06* | (2006.01) |
| *C07K 16/12* | (2006.01) |
| *A61K 39/00* | (2006.01) |

(52) U.S. Cl.
CPC ............ *C12Q 1/6897* (2013.01); *A61K 39/40* (2013.01); *A61K 45/06* (2013.01); *C07K 16/12* (2013.01); *G01N 33/6893* (2013.01); *A61K 2039/505* (2013.01); *G01N 2333/195* (2013.01); *G01N 2800/042* (2013.01)

(58) Field of Classification Search
None
See application file for complete search history.

(56) References Cited

U.S. PATENT DOCUMENTS

2012/0135957 A1* 5/2012 Dugenet ............... A23L 1/0528
514/54

FOREIGN PATENT DOCUMENTS

WO   WO 2012024638 A2 *   2/2012

OTHER PUBLICATIONS

Duck et al. Inflammatory Bowel Diseases 13: 1191-1201, 2007, abstract.*
Altschul, S. et al., "Basic Local Alignment Search Tool" J. Mol. Biol. (1990) pp. 403-410, vol. 215.
Andersen, J.B. et al., "New Unstable Variants of Green Fluorescent Protein for Studies of Transient Gene Expression in Bacteria" Appl. Environ. Microbiol (Jun. 1998) pp. 2240-2246, vol. 64, No. 6.
Carvalho, F.A. et al., "Transient Inability to Manage Proteobacteria Promotes Chronic Gut Inflammation in TLR5-Deficient Mice" Cell Host Microbe (Aug. 2012) pp. 139-152, vol. 12.
Carvalho, F.A. et al., "Cytosolic flagellin receptor NLRC4 protects mice against mucosal and systemic challenges" Mucosal Immunol. (May 2012) pp. 288-298, vol. 5, No. 3.
Davis, L.M.G. et al., "A dose dependent impact of prebiotic galactooligosaccharides on the intestinal microbiota of healthy adults" Int. J. Food Microbiol. (2010) pp. 285-292, vol. 144.
Edgar, R.C. et al., "Uchime improves sensitivity and speed of chimera detection" Bioinformatics (2011) pp. 2194-2200, vol. 27, No. 16.
Feng, T. et al., "Microbiota innate stimulation is a prerequisite for T cell spontaneous proliferation and induction of experimental colitis" J. Exp. Med. (2010) pp. 1321-1332, vol. 207, No. 6.
Ferrari, S.L. et al., "Beta Regression for Modelling Rates and Proportions" Journal of Applied Statistics (Aug. 2004) pp. pp. 799-815, vol. 31, No. 7.
Forbes, S.J. et al., "Inhibition of *Salmonella enterica* Serovar Typhimurium Motility and Entry into Epithelial Cells by a Protective Antilipopolysaccharide Monoclonal Immunoglobulin A Antibody" Infect. Immun. (Sep. 2008) pp. 4137-4144, vol. 76, No. 9.
Friman, V. et al., "Decreased Expression of Mannose-Specific Adhesins by *Escherichia coli* in the Colonic Microflora of Immunoglobulin A-Deficient Individuals" Infect. Immun. (Jul. 1996) pp. 2794-2798, vol. 64, No. 7.
Gewirtz, A.T. et al., "Dominant-negative TLR5 polymorphism reduces adaptive immune response to flagellin and negatively associates with Crohn's disease" Am. J. Physiol. Gastrointest. Liver Physiol. (2006) pp. G1157-G1163, vol. 290.
Gong, Y. et al., "Sensing bacterial infections by NAIP receptors in NLRC4 inflammasome activation" Protein Cell (2012) pp. 98-105, vol. 3, No. 2.
Halff, E. et al., "Formation and Structure of a NAIP5-NLRC4 Inflammasome Induced by Direct Interactions with Conserved N- and C-terminal Regions of Flagellin" J Biol Chem (Nov. 2012) pp. 38460-38472, vol. 287, No. 46.
Hamady, M. et al., "Error-correcting barcoded primers for pyrosequencing hundreds of samples in multiplex" Nat. Methods (Mar. 2008) pp. 235-237, vol. 5, No. 3.

(Continued)

*Primary Examiner* — S. Devi
(74) *Attorney, Agent, or Firm* — Scully Scott Murphy & Presser

(57) ABSTRACT

High levels of bacterial flagella in a sample such as a gastrointestinal sample and/or low levels of anti-flagella antibodies serve as an indication for metabolic syndrome (such as insulin resistance, hypertension, elevated cholesterol, increased risk for blood clotting, and obesity) with highest levels of adiposity. An intervention that reduces the level and/or activity of flagella in the gastrointestinal tract can mitigate the severity of metabolic syndrome or in protecting against the development of metabolic syndrome.

**10 Claims, 10 Drawing Sheets
(6 of 10 Drawing Sheet(s) Filed in Color)**

(56) References Cited

OTHER PUBLICATIONS

Hapfelmeier, S. et al., "Reversible Microbial Colonization of Germ-Free Mice Reveals the Dynamics of IgA Immune Responses" Science (Jun. 2010) pp. 1705-1709, vol. 328.
Hayashi, F. et al., "The innate immune response to bacterial flagellin is mediated by Toll-like receptor 5" Nature (Apr. 2001) pp. 1099-1103, vol. 410.
Huson, D.H. et al., "MEGAN analysis of metagenomic data" Genome Res. (2007) pp. 377-386, vol. 17.
Koren, O. et al., "Human oral, gut, and plaque microbitoa in patients with atherosclerosis" Porc. Natl. Acad. Sci. USA (Mar. 2011) pp. 4592-4598, vol. 108, No. 1.
Kundu, T.K. et al., "Promoter selectivity of *Escherichia coli* RNA polymerase sigmaF holoenzyme involved in transcription of flagellar and chemotaxis genes" Journal of Bacteriology (1997) pp. 4264-4269, vol. 179, No. 13.
Kurokawa, K. et al., "Comparative Metagenomics Revealed Commonly Enriched Gene Sets in Human Gut Microbiomes" DNA Ressearch (2007) pp. 169-181, vol. 14.
Letran, S.E. et al., "TLR5 functions as an endocytic receptor to enhance flagellin-specific adaptive immunity" Eur. J. Immunol. (2011) pp. 29-38, vol. 41.
Lonnermark, E. et al., "Oral and faecal lactobacilli and their expression of mannose-specific adhesins in individuals with and without IgA deficiency" Inst. J. Med. Microbiol. (2012) pp. 53-60, vol. 302.
McDonald, D. et al., "An improved Grenngenes taxonomy with explicit ranks for ecological and evolutionary analyses of bacteria and archaea" ISME J. (2012) pp. 610-618, vol. 6.
Meyer, F. et al., "The metagenomics RAST server-a public resource for the automatic phylogenetic and functional analysis of metagenomes" BMC Bioinformatics (2008) pp. 386-393, vol. 9.
Miao, E. et al., "TLR5 and Ipaf: dual sensors of bacterial flagellin in the innate immune system" Semin. Immunopathol. (2007) pp. 275-288, vol. 29.
Newton, S. et al., "Immune Response to Cholera Toxin Epitope Inserted in *Salmonella flagellin*" Science (Apr. 1989) pp. 70-72, vol. 244.
Peterson, D.A. et al., "IgA Response to Symbiotic Bacteria as a Mediator of Gut Homeostasis" Cell Host Microbe (Nov. 2007) pp. 328-339, vol. 2.
Prakash, T. et al., "Complete genome Sequesnces of Rat and Mouse segmented filamentous bacteria a potent inducer of Th17 cell differentiation" Cell Host Microbe (Sep. 2011) pp. 273-284, vol. 10.
Saldanha, A.J., "Java Treeview-extensible visualization of microarray data" Bioinformatics (2004) pp. 3426-3248, vol. 20, No. 17.
Salim, S. et al., "Importance of Disrupted Intestinal Barrier in Inflammatory Bowel Diseases" Inflamm. Bowel. Dis. (Jan. 2011) pp. 362-381, vol. 17, No. 1.
Sitaraman, S. et al., "Elevated flagellin-specific immunoglobulins in Crohn's disease" Am. J. Physiol. Gastrointest. Liver Physiol. (2005) pp. G403-G406, vol. 288.
Spector, T.D. et al., "The UK Adult Twin Registry (TwinsUK)" Twin Res. Hum. Genet. (2006), pp. 899-906, vol. 9, No. 6.
Stewart, F.J. et al., "Development and quantitative analyses of a universal rRNA-subtraction protocol for microbial metatranscriptomics" ISME J. (2010) pp. 896-907, vol. 4.
Turnbaugh, P.J. et al., "An obesity-associated gut microbiome with increased capacity for energy harvest" Nature (Dec. 2006) pp. 1027-1031, vol. 444.
Turner, J., "Intestinal Mucosal barrier function in health and disease" Nat. Rev. Immunol. (Nov. 2009) pp. 799-809, vol. 9.
Van Der Waaij, L.A. et al., "In vivo IgA coating of anareobic bacteria in human faeces" Gut (1996) pp. 348-354, vol. 38.
Verberkmoes, N.C. et al., "Shotgun metaproteomics of the human distal gut microbiota" ISME J. (2009) pp. 179-189, vol. 3.
Vijay-Kumar, M. et al., "Metabolic Syndrome and Altered Gut Microbiota in Mice Lacking Toll-Like Receptor 5" Science (Apr. 2010) pp. 228-231, vol. 328.
Ziegler, T.R. et al., "Detectable Serum flagellin and lipopolysaccharide and upregulated anti-flagellin and lippolysaccharide immunoglobulins in human shot bowl syndrome" Am. J. Physiol Regul Inger Comp Physil (2008) pp. 1-18, vol. 294, No. 2: R402-R410.
Lodes, M.J. et al., "Bacterial flagellin is a dominant antigen in Crohn disease" The Journal of Clinical Investigation (2004) pp. 1296-1306, vol. 113, No. 9.
International Search Report dated Jun. 20, 2013 issued in International Application No. PCT/US2013/029050.

* cited by examiner

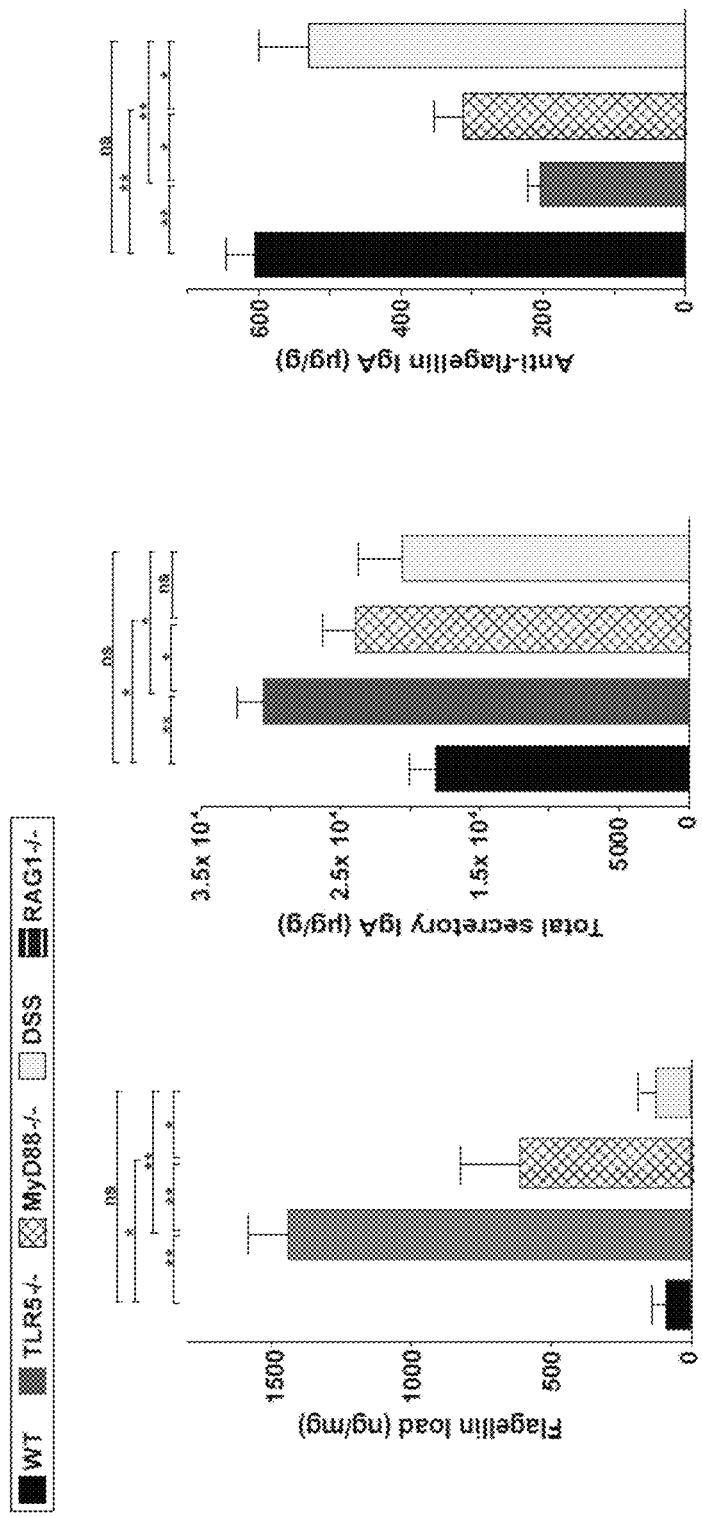

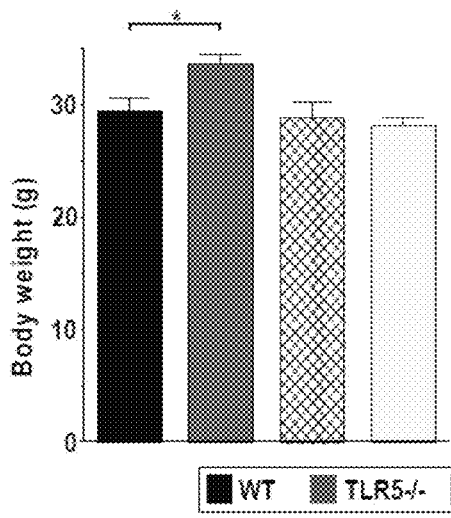
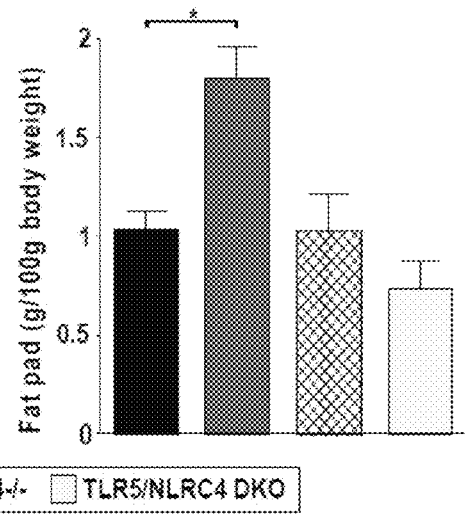
FIG. 4A  FIG. 4B
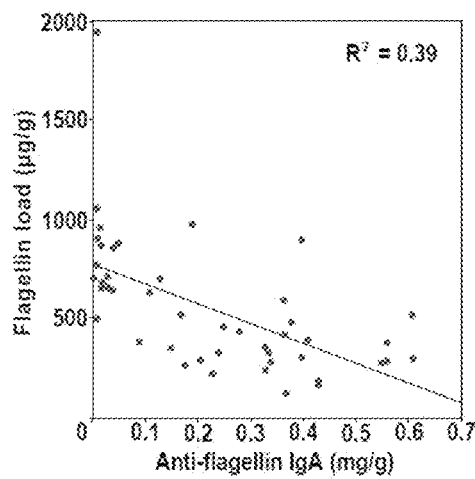
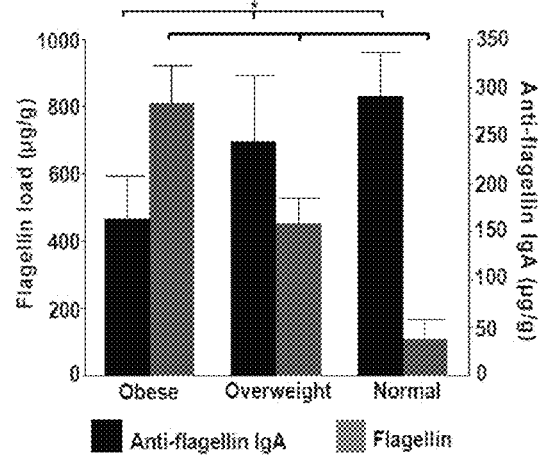
FIG. 4C  FIG. 4D

US 9,885,089 B2

FLAGELLUM AND ANTI-FLAGELLUM ANTIBODY LEVELS IN SAMPLES AS A DIAGNOSTIC BIOMARKER AND THERAPEUTIC TARGET FOR METABOLIC SYNDROME

CROSS REFERENCE TO RELATED APPLICATIONS

This application claims priority from U.S. Provisional Application No. 61/606,522, filed Mar. 5, 2012, the entire contents of which are incorporated herein by reference.

STATEMENT REGARDING FEDERALLY SPONSORED RESEARCH OR DEVELOPMENT

This invention was made with Government support under contract #R01DK093595 and DP2OD007444 awarded by the National Institutes of Health. The Government has certain rights in this invention.

INCORPORATION BY REFERENCE OF SEQUENCE LISTING

The Sequence Listing in an ASCII text file, named as 28612_5828_03_US_SequenceListing.txt of 1 KB, created on Sep. 4, 2014, and submitted to the U.S. Pat. and Trademark Office via EFS-Web, is incorporated herein by reference.

FIELD OF THE DISCLOSURE

This invention relates to biomarkers and therapeutics for metabolic syndrome. In particular, levels of bacterial flagella and antibodies directed thereto in a sample, such as a gastrointestinal tract sample, have been identified herein to be associated with metabolic syndrome in humans, and serve as a therapeutic target for treating metabolic syndrome.

BACKGROUND ART

Today, health problems associated with obesity are some of the most daunting in the United States. Gut microbiota, microorganisms that live in the digestive tract, are one of the triggers of metabolic syndrome (insulin resistance, hypertension, elevated cholesterol, increased risk for blood clotting, and obesity). While we are born germ-free from a sterile womb, our intestinal tract is rapidly colonized by microbes like bacteria, fungi, and even protozoan parasites, which collectively become our microbiome. From birth until we reach adulthood, our intestine carries about ten times as many microorganisms as all the cells in the rest of our body.

The adult human host produces roughly 6-10 grams of secretory immunoglobulin A (SIgA) into the gut lumen daily, where it binds 30-50% of the $10^{13}$-$10^{14}$ microbes that inhabit the intestine. As a consequence, a significant portion of microbial cells in the lumen is coated with IgA, a smaller fraction with IgG and IgM. The majority of this IgA is thought to be relatively unselective as it binds antigens that are widely shared amongst gut bacteria, including bacterial flagellum and lipopolysaccharide (LPS).

The gut microbiota can trigger metabolic and inflammatory disease. Transplantation of gut microbiota from affected mice and humans transfers excess adiposity, colitis, and metabolic syndrome to naïve germ-free hosts (Feng et al., *J. Exp. Med.* 207:1321 (2010); Turnbaugh et al., *Nature* 444: 1027 (2006) and Vijay-Kumar et al., *Science* 328:228 (2010)). Two main mechanisms have been described to explain how microbiota can influence host metabolism: bacterial community composition can affect the efficiency of energy extraction from the diet, liberating excess energy for the host (Turnbaugh et al., *Nature* 444:1027 (2006)), and alternatively, microbiota can trigger metabolic inflammation leading to reduced insulin sensitivity (Vijay-Kumar et al., *Science* 328:228 (2010)). It has been shown that the microbiota of mice deficient in Toll-like receptor (TLR) 5 induce metabolic inflammation when transferred to wildtype (WT) germ-free recipients, and that this inflammatory microbiome is less temporally stable, and more enriched in Proteobacteria, compared to WT microbiota (Vijay-Kumar et al., *Science* 328:228 (2010)). However, the elements of the microbiota that raise its inflammatory potential remain unclear.

SUMMARY OF THE DISCLOSURE

It has been discovered by the inventors that levels of bacterial flagella and anti-flagella antibodies in the gastrointestinal tract are indicative of metabolic syndrome. In particular, it has been demonstrated herein that a wide diversity of gut bacteria produce excess levels of flagellin in the gut of TLR5-deficient mice, which harbor a gut microbiota that trigger metabolic syndrome. It has also been demonstrated that the production of anti-flagellin antibodies (IgA and IgG) is impaired in the absence of TLR5, and that anti-flagellin IgA directly downregulates flagella production. Bacterial flagellin load has been found herein to be inversely proportional to anti-flagellin IgA levels in various mouse and human gut samples. Furthermore, high fecal flagellin load has been found therein to be associated with obesity in humans. These observations indicate that in normal gut homeostasis, anti-flagellin IgA quenches bacterial flagellar motility, thereby preventing the intestinal inflammation associated with various chronic disease conditions including metabolic syndrome. An intervention that reduces levels of flagella in the gastrointestinal tract can reduce flagella levels, and mitigate the severity of metabolic syndrome or protect against the development of metabolic syndrome. Accordingly, this disclosure is directed to methods useful for diagnosing, monitoring, and treating metabolic syndrome.

In one aspect, this disclosure provides a method of diagnosing metabolic syndrome based on detecting the levels of flagella and/or anti-flagella antibodies in a sample.

In some embodiments, the sample is a gastrointestinal tract sample or "GI" sample, such as a fecal, intestinal or mucosal sample, or an oral sample. In other embodiments, other samples, such as samples of body fluids (e.g., blood or urine) can be used as well.

In one embodiment, the present method is based on detection of anti-flagellin antibodies in a GI sample, and diagnosis of metabolic syndrome is based on a decreased level of anti-flagellin antibodies as compared to control. Anti-flagellin antibodies can be detected directly or indirectly using an antigen, such as flagellin or an immunogenic peptide fragment of a flagellin, in an assay of suitable format (e.g., ELISA).

In another embodiment, the present method is based on detection of flagellin in a GI sample, and diagnosis of metabolic syndrome is based on an increased level of flagellin as compared to control. Flagellin can be detected directly or indirectly using an agent that specifically binds to flagellin, such as anti-flagellin antibodies, or other molecules that specifically bind flagellin (e.g., TLR5 or receptors that form part of the NLRC4 inflammasome), in an assay of suitable format (e.g., a cell-based assay).

In a further aspect, this disclosure provides a method of treating a subject diagnosed to have metabolic syndrome, comprising administering to the subject a therapeutic agent which reduces the level or activity of flagella. Suitable therapeutic agents include can be a protein (such as, e.g., an antibody specific for flagellin), an aptamer, a small molecule compound, or other molecules which reduce the levels and/or activities of flagella, or which induces higher levels of anti-flagella antibodies.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

FIGS. 1A-1D. Flagellin load and flagella-related genes are inversely proportional to anti-flagellin IgA in TLR5−/− and WT mice. (A) Metatranscriptome analysis. cDNAs assigned to the 18 most significant COG categories were normalized and hierarchically clustered. Dendrogram (bottom) shows clustering of samples based on the uncentered correlation similarity metric. Correlation coefficients are represented by color ranging from blue (−5× depletion relative to mean values across genotypes) to yellow (533 enrichment). Metagenomic reads from the same 18 COG categories were processed similarly. Functional categories are indicated in the legend; flagella-associated gene categories are highlighted in red. (B) Flagellin load. (C) Total IgA load. (D) Flagellin-specific IgA. Bars are means ±s.e. N=5-8 mice/group; *P<0.01,**P<0.001; two-tailed t-test; n.s., non-significant.

FIGS. 4A-4D. NLRC4 is required for metabolic syndrome in TLR5−/− mice and flagellin load in feces is inversely correlated with anti-flagellin IgA in humans. (A) Total body weight. (B) Fat pad weight as a percentage of total body weight. N=5-6 mice/group. *P<0.05; two-tailed t-test. (C) Flagellin load correlated with anti-flagellin IgA levels for human stool samples. (D) Means ±s.e. for subjects with normal (18.5-24.9, N=17), overweight (25-29.9, N=11) and obese (>30, N=15) BMIs. *P<0.05; one-way analysis of variance (ANOVA).

DETAILED DESCRIPTION

Diagnostic Marker and Methods

Figure 1A:
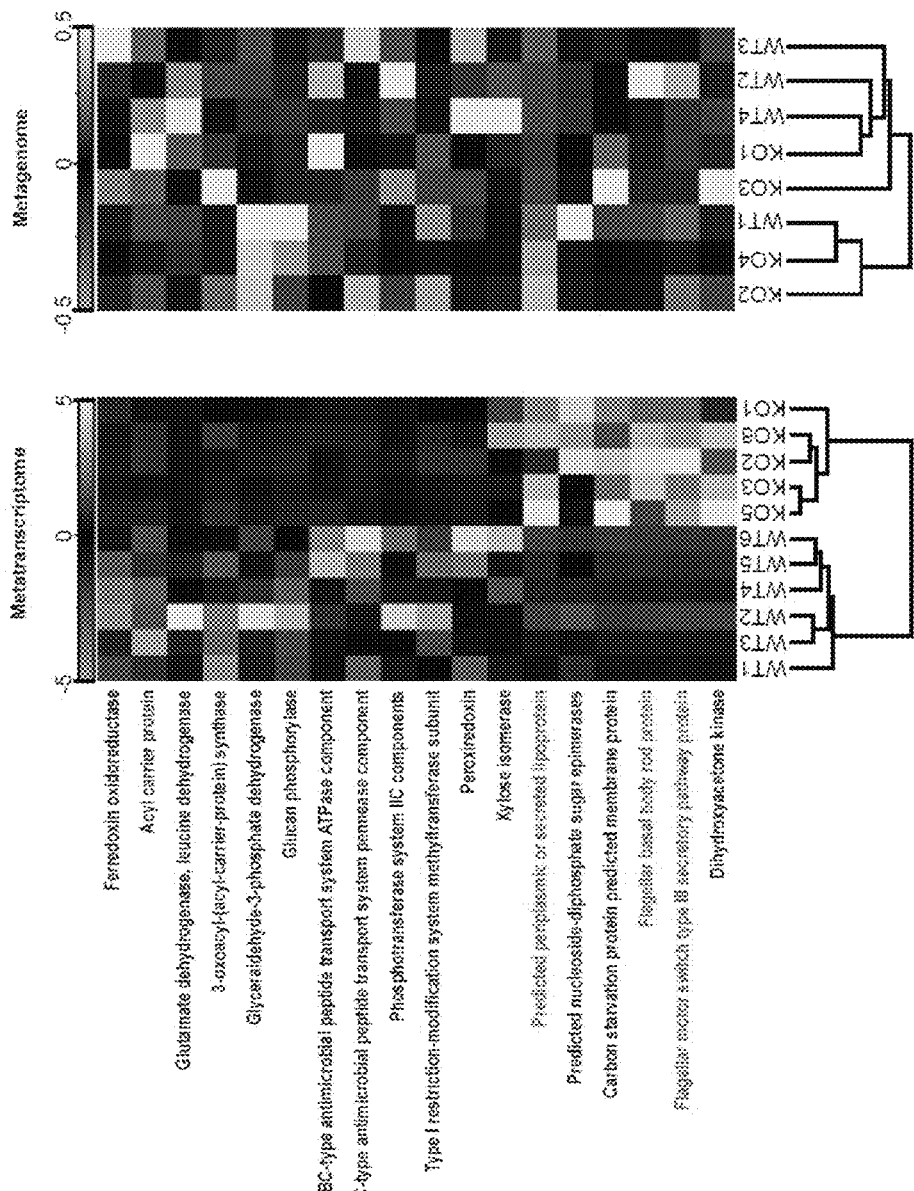

It has been discovered by the inventors that high levels of bacterial flagella, and low levels of anti-flagella antibodies, are associated with metabolic syndrome. Therefore, in one aspect, this disclosure is directed to detection of flagella and anti-flagella antibody in a sample as a biomarker for metabolic syndrome in a subject, particularly a human subject.

The term "metabolic syndrome", as used herein, refers to a combination of abnormalities found in an individual that are associated with increased risk for the development of type 2 diabetes and atherosclerotic vascular disease (e.g., heart disease and stroke). The abnormalities can include two or more of: raised blood pressure, raised triglycerides level, reduced HDL level, raised fasting plasma glucose level, insulin resistance, and obesity, particularly central obesity.

In accordance with the present invention, the levels of flagella and anti-flagella antibodies in a sample can serve as a biomarker for metabolic syndrome, including particularly obesity, independent of other indicators of metabolic syndrome described above. Thus, the levels of flagella and/or the levels of anti-flagella antibodies can be used alone as basis to diagnose metabolic syndrome, or used to aid in the diagnosis of metabolic syndrome, or to monitor the efficacy of a therapeutic regimen of metabolic syndrome. Given that the bacterial flagellum is made up of the protein flagellin, the determination is equally made by measurement of the levels of flagellin and/or the levels of anti-flagellin antibodies.

In many embodiments, the method is based on detection using a gastrointestinal tract sample or "GI" sample. In other embodiments, other samples, such as samples of body fluids (e.g., blood or urine) can be used as well.

By "gastrointestinal sample" it is meant herein a sample containing or reflecting the contents of the gastrointestinal tract, including, for example, a fecal, intestinal or mucosal sample. The term "gastrointestinal tract" refers to the digestive tract stretching from the mouth to anus, excluding the accessory glandular organs. Thus, a GI sample, as used herein, also includes an oral sample, such as a tooth or cheek scraping or saliva.

In some embodiments, the present method is based on detection of anti-flagellin antibodies in a GI sample.

Anti-flagellin antibodies include antibodies to any flagellin. For example, flagellin can be from any flagellated bacteria, including but not limited to bacterial species of Firmicutes (such as *Roseburia* spp. and *Clostridum* spp.), and Proteobacteria (such as *E. coli* or *Salmonella typhimurium*). The antibodies, as used herein, encompass all immunoglobulin isotypes including, for example, immunoglobulin A and G.

Anti-flagellin antibodies can be detected directly or indirectly using an antigen, such as flagellin or an immunogenic peptide fragment of a flagellin. Generally, a peptide should be at least 5-6 amino acid in length, or at least 7, 8 or 9 amino acid in length, to be immunogenic. The antigen can be provided in a purified or substantially purified form in a solution, bound to a solid support (such as beads, chips, chromatography matrices, or microtiter plates), or expressed from whole cells or a phage display system, suitable for binding and detection of antibodies.

In a specific embodiment, anti-flagellin antibodies are detected in an enzyme-linked immunosorbent assay (ELISA) using flagellin coated to an ELISA plate (see Example 2). In another embodiment, anti-flagellin antibodies are detected in a flow cytometry analysis using flagellin-coated beads. In still another embodiment, phage particles expressing a flagellin or a fragment thereof can be anchored, for example, to a multiwell plate via an antiphage antibody.

In immunoassays such as ELISA, the anti-flagellin antibodies captured by the antigen can be detected by using a secondary antibody, which can be specific for anti-flagellin antibodies or for the constant region of human immunoglobulins. The secondary antibody can be conjugated to an agent which provides a detectable signal or is capable of producing a detectable signal. For example, the agent can be an enzyme such as horseradish peroxidase (HRP), alkaline phosphatase (AP), beta-galactosidase or urease, all of which are well known to generate a detectable signal when used in conjunction with an appropriate substrate. Secondary antibodies linked to an enzymatic agent are readily available from various commercial sources. Alternatively, the agent can be a chemiluminescent marker. Secondary antibodies labeled with a chemiluminescent marker also can be obtained commercially from various sources. Alternatively, the agent can be a fluorochrome such as DAPI, fluorescein, Hoechst 33258, R-phycocyanin, B-phycoerythrin, R-phycoerythrin, rhodamine, Texas red or lissamine. A particularly useful fluorochrome is fluorescein or rhodamine. Secondary antibodies linked to fluorochromes can be obtained commercially as well.

Signals from a detectable agent can be analyzed and quantified, and the levels of anti-flagellin antibodies can be determined. The level of anti-flagellin antibodies in a sample under examination can be compared with a control level to determine whether the subject under examination has metabolic syndrome. The comparison can be directed to specific isotyes, e.g., either IgA or IgG, or a combination of multiple isotypes (e.g., IgA and IgG), or combination of all isotypes.

The control level represents the level of anti-flagellin antibodies in a normal individual without metabolic syndrome, or a range of levels in a normal population without metabolic syndrome. The control level can be a predetermined value or range of values, or determined side-by-side with the subject under examination. Generally speaking, in normal individuals without metabolic syndrome, the levels of anti-flagellin IgA are 700 ug/g or higher, and the levels of anti-flagellin IgG are 700 ng/g or higher. When the level of anti-flagellin antibodies in a test sample is substantially lower than the control level or is below the range of control levels, the individual is determined to have metabolic syndrome. By "substantially lower", it is meant at least 10%, 15% or more, lower than the control level.

In other embodiments, the levels of flagellin in a GI sample is being detected and measured.

Flagellin can be detected directly or indirectly using an agent that specifically binds to flagellin, such as anti-flagellin antibodies, or other molecules that specifically bind flagellin. Examples of such other molecules include Toll-like receptor 5 (TLR5), one or more receptors that form part of the (Nod-like receptor) family, CARD (Caspase activation and recruitment domain)-containing 4 (NLRC4) inflammasome (e.g., one or both of NAIP5 and NLCR4 receptors, as described in e.g., Halff et al., *J Biol Chem* 287(46):38460-38472 (2012); see also, review by Gong et al., *Protein Cell* 3: 98-105 (2012)), or aptamers that bind flagellin.

In a specific embodiment, flagellin in a GI sample is detected in a cell-based assay using a cell line which expresses TLR5 and/or one or more flagellin receptors that form part of the NLRC4 inflammasome.

A variety of cell lines are available and suitable for expression and cell surface display of TLR5 and/or flagellin receptors that form part of the NLRC4 inflammasome. Examples of suitable cell lines include various mammalian cell lines, for example, mammalian fibroblast cell lines such as COS cells, NIH-3T3, HEK293, among others. A cell line can be transformed with an expression vector that encodes and expresses TLR5 and/or one or more flagellin receptors that form part of the NLRC4 inflammasome, which in a specific embodiment, can be human or mouse TLR5 and/or one or more flagellin receptors that form part of the NLRC4 inflammasome.

In order to detect flagellin, a TLR5 and/or one or more flagellin receptors that form part of the NLRC4 inflammasome expressing cell line is also transformed with a reporter gene which upon binding of TLR5 and/or one or more flagellin receptors that form part of the NLRC4 inflammasome by flagellin, generates a detectable signal. The reporter gene can encode an enzyme, for example, SEAP (secreted alkaline phosphatase), β-galactosidase gene (lacZ gene), and luciferase. The reporter gene can also encode a fluorescent protein, such as GFP (green fluorescent protein).

The reporter gene is preferably placed on a reporter gene plasmid under the control of an inducible promoter. The inducible promoter is selected from those which can be induced by a transcription factor that is a component of the TLR-induced intracellular signal cascade, for example, nuclear factor kappa-B (NF-κB), the NLRC4 inflammasome, and caspase-1. Examples of NF-κB inducible promoters include selectin and ELAM-1 (endothelial cell leukocyte adhesion molecule-1) promoters, which contains an NF-κB response element. Other suitable promoters include those that contain a nucleic acid element responsive to (bound and activated by) the NLRC4 inflammasome or caspase-1.

On activation of TLR5 as a result of flagellin binding, NF-κB localized in the cytoplasm is released and translocated into the cell nucleus, and activates the inducible promoter which leads to the expression of the reporter gene and the generation of a detectable signal.

Detection of flagellin in a sample can be achieved by mixing the sample and the TLR5-expressing cell (and/or a cell expressing one or more flagellin receptors that form part of the NLRC4 inflammasome) which contains an inducible reporter gene, and incubating the sample-cell mixture to induce the expression of the reporter gene. Subsequently, the induced sample-cell mixture, or the supernatant thereof, is mixed with a detection medium, and the resulting mixture is incubated under suitable conditions to generate a detectable signal. In cases where the reporter gene encodes an enzyme, the detection medium contains a substrate for the enzyme. Quantification of the signal, e.g., the enzymatically converted substrate, permits a determination of the level or concentration of flagellin in the sample.

In one embodiment, the reporter gene encodes an alkaline phosphatase, preferably, a secreted alkaline phosphatase (SEAP), and the detection medium contains 5-Bromo-4-chloroindolyl phosphate (BCIP) as substrate. Detection of the enzyme activity occurs by the blue color change and/or blue precipitate. In another embodiment, the reporter gene encodes an alkaline phosphatase, and the detection medium contains p-nitrophenyl phosphate (pNPP) as substrate. The alkaline phosphatase activity is indicated by hydrolytic cleavage of pNPP by the yellow color change of the solution. The yellow color change of the solution can be detected and quantified photometrically.

In another embodiment, the reporter gene encodes β-galactosidase activity and the detection medium contains 5-bromo-4-chloro-3-indolyl-β-D-galactopyranoside (X-Gal) as substrate. Detection of enzyme activity occurs by the blue color change and/or blue precipitate.

In another embodiment, the reporter gene encodes luciferase and the detection medium contains luciferin as substrate. In the presence of optionally added ATP and $Mg^{2+}$ the enzyme activity is indicated by luminescence (chemiluminescence assay).

Therapeutic Methods

The inventors believe that in normal gut homeostasis, anti-flagellin IgA quenches bacterial flagellar motility, thereby preventing the intestinal inflammation associated with metabolic syndrome. An intervention that reduces levels or activity of flagella in the gastrointestinal tract can mitigate the severity of metabolic syndrome or protect against the development of metabolic syndrome. Accordingly, this disclosure provides methods for preventing or delaying the onset, or reducing the severity of metabolic syndrome in a subject by reducing levels or activity of bacterial flagella in the gastrointestinal (GI) tract.

The subject to which the therapeutic intervention is applied to can be a subject having metabolic syndrome, determined either on the basis of the levels of flagellin or anti-flagellin in a sample as described above, or on the basis of other parameters. Additionally, the subject to which the therapeutic intervention is applied to can be a subject at risk of developing metabolic syndrome.

In accordance with the present methods, a therapeutic agent which can reduce levels and/or activities of bacterial flagella can be administered to the subject in need of the treatment. The therapeutic agent can be a protein (such as, e.g., an antibody specific for flagellin), an aptamer, a small molecule compound, or other molecules which reduce the levels and/or activities of flagella, for example. Assays for determining whether a particular agent reduces the level (e.g., via inhibiting the expression) or the activity of flagellin (e.g., bacterial motility) are illustrated herein below in the Examples section.

In one embodiment, an anti-flagellin antibody or a functional fragment thereof is administered to a subject in need of the treatment. Antibodies suitable for use in the therapeutic methods include both monoclonal antibodies and polyclonal antibodies, as well as single chain antibodies, chimeric antibodies and humanized antibodies, and can be of any class of immunoglobulins, such as IgG, IgM, IgA, IgD or IgE, particularly IgA and/or IgM, and the subclass thereof. By "functional fragment" it is meant an antigen-binding portion of an immunoglobulin molecule, which typically includes the heavy and light chain variable regions of an antibody molecule, for example, Fab, Fab', or $F(ab')_2$. Suitable antibodies can be produced in a non-human mammal, including for example, rabbits, rats, mice, horses, goats, camels, or primates. Monoclonal antibodies produced from a non-human mammal can be humanized to reduce the immunogenicity for use in humans following techniques documented in the art. For example, to humanize a monoclonal antibody raised in mice, one approach is to make mouse-human chimeric antibodies having the original variable region of the murine mAb, joined to constant regions of a human immunoglobulin. Alternatively, humanized antibodies can be made by including constant regions of a human immunoglobulin, and additionally, substituting framework residues of the variable regions of a non-human antibody with the corresponding human framework residues, either leaving the non-human CDRs substantially intact, or even replacing the CDR with sequences derived from a human genome. As an additional alternative, human antibodies can be produced from transgenic animals (e.g., transgenic mice) whose immune systems have been altered to correspond to human immune systems.

In another embodiment, an aptamer that binds specifically to flagellin is administered to a subject in need of the treatment. Aptamers are molecules, either nucleic acid or peptide, that bind to a specific target molecule. Nucleic acid aptamers are generally short strands of DNA or RNA that have been engineered through repeated rounds of in vitro selection known as SELEX (systematic evolution of ligands by exponential enrichment) to bind to various molecular targets. Peptide aptamers can be selected using various systems, most frequently through the yeast two hybrid system. Peptide aptamers generally consist of a variable peptide loop (typically composed of ten to twenty amino acids), attached at both ends to a protein scaffold. This double structural constraint greatly increases the binding affinity of the peptide aptamer to levels comparable to an antibody.

In still another embodiment, a small molecule compound that reduces the level and/or activity of flagella is administered to a subject in need of the treatment. Small molecules include organic compounds, organometallic compounds, salts of organic and organometallic compounds, saccharides, amino acids, and nucleotides. Small molecules typically have molecular weights less than approximately 1000 Daltons, in some embodiments less than 800 Daltons. Small molecules include compounds that are found in nature as well as synthetic compounds. Small molecules useful for use in the present methods can be discovered by methods well known in the art, for example, screening a library of small molecule compounds for those that reduce the level and/or activity of flagella.

In other embodiments, an agent that induces higher levels of anti-flagella antibodies is administered to a subject in need of the treatment, to ameliorate the severity of metabolic syndrome or to prevent or delay the onset of metabolic syndrome. Examples of agents suitable for use in this approach include flagellin peptide fragments, probiotic organisms genetically engineered to produce flagellin peptide fragments, for example.

A therapeutic agent described above can be combined with a pharmaceutically acceptable carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like.

As used herein, a pharmaceutically acceptable carrier includes any and all solvents, dispersion media, isotonic agents and the like. Except insofar as any conventional media, agent, diluent or carrier is detrimental to the recipient or to the effectiveness of the active ingredients contained therein, its use in practicing the methods disclosed herein is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

The concentration of a therapeutic in formulations may range from as low as about 0.1% to as much as 15 or 20% by weight and can be selected based on the nature of the particular agent used, the mode of administration selected, among other considerations. A typical formulation for injection could be made up to contain 1 mL sterile buffered water of phosphate buffered saline and 1-1000 mg, possibly 10-100 mg, of an agent such as an antibody, for example. The amount of an agent administered to be effective may depend on the condition of the patient (e.g., age, body weight and severity of metabolic syndrome), and the nature of the agent. The precise amount of an agent to be effective can be determined by a skilled physician.

A pharmaceutical formulation containing a therapeutic agent can be given to a subject by any standard route, including ingestion, or injections via an intravenous, intraperitoneal, subcutaneous, transdermal, intramuscular, intranasal, or sublingual route.

The present description is further illustrated by the following examples, which should not be construed as limiting in any way. The contents of all cited references (including literature references, issued patents, and published patent applications as cited throughout this application) are hereby expressly incorporated by reference.

EXAMPLE-1

In this Example, the inventors used metatranscriptomics to show that a wide diversity of gut bacteria produce excess levels of flagellin in the TLR5-deficient gut. The inventors found that the production of anti-flagellin antibodies (IgA and IgG) was impaired in the absence of TLR5, and that anti-flagellin IgA directly downregulated flagella production. Consistent with this, bacterial flagellin load was inversely proportional to anti-flagellin IgA levels in various mouse and human gut samples. Furthermore, high fecal flagellin load was associated with obesity in humans. The results indicate that in normal gut homeostasis, anti-flagellin IgA quenches bacterial flagellar motility, thereby preventing the intestinal inflammation associated with many different chronic disease conditions.

The inventors used a combined shotgun metatranscriptomics and metagenomics approach to characterize the functional differences between the TLR5−/− and WT microbiomes (Table 1). Unsupervised hierarchical clustering of samples based on the enrichment or depletion of conserved orthologous groups (COGs) of genes segregated the metatranscriptomes, but not the metagenomes, by host genotype. This finding indicates that the functional capacities of the microbiomes are similar between TLR5−/− and WT mice, but the gene expression patterns differ substantially (FIG. 1A). Remarkably, 3 of the 6 COGs with upregulated expression in TLR5−/− mice were related to flagellar motility. Taxonomic assignments showed flagella-associated genes in the TLR5−/− microbiota were expressed by two main groups: butyrate-producing Firmicutes (e.g., *Roseburia, Eubacterium, Clostridium*), and Proteobacteria (e.g., *Desulfovibrio* spp.).

TABLE 1

Number of sequences generated for the metagenomic and metatranscriptomic analyses. Sequences were generated the 454 Titanium and Illumina HiSeq2000 sequencing platforms. Values are linked to their corresponding samples on the MG-RAST server.

| Metagenome | | Metatranscriptome | |
|---|---|---|---|
| 454 Titanium | | Illumina HiSeq2000 | |
| WT1 | 62,079 WT1 | 50,265,870 WT1 | 385,818 |
| WT2 | 81,981 WT2 | 36,401,312 WT2 | 867,363 |
| WT3 | 59,515 WT3 | 31,012,847 WT3 | 289,619 |
| WT4 | 74,533 WT4 | 53,119,526 WT4 | 389,702 |
| TLR5-/-1 | 55,151 TLR5-/-1 | 29,535,962 WT5 | 632,651 |
| TLR5-/-2 | 73,413 TLR5-/-2 | 33,884,214 WT6 | 1,058,677 |
| TLR5-/-3 | 64,550 TLR5-/-3 | 14,850,852 TLR5-/-1 | 1,236,202 |
| TLR5-/-4 | 27,581 TLR5-/-4 | 38,445,732 TLR5-/-2 | 2,230,754 |
| | | TLR5-/-3 | 2,669,913 |
| | | TLR5-/-4 | 289,402 |
| | | TLR5-/-5 | 756,732 |

To verify that the greater transcription of flagella-associated genes in the TLR5−/− host resulted in elevated levels of flagella, the inventors estimated flagellin load using a TLR5-reporter cell assay. It was observed that flagellin levels, which were standardized using flagellin from *Salmonella typhimurium*, were significantly elevated in the cecal contents and fecal pellets of TLR5−/− mice and stable over time (FIG. 1B). Flagellin levels were also high in MyD88−/− mice, which have impaired TLR5 signaling (Hayashi et al., *Nature* 410:1099 (2001)). Increased flagellin was not simply a consequence of low-grade inflammation because flagellin levels in WT mice with chemically-induced inflammation (dextran sulfate sodium (DSS)) were equivalent to those of non-inflamed WT. Though segmented filamentous bacteria (SFB) possess genes for flagella (Prakash et al., *Cell Host Microbe* 10:273 (2011)), the inventors did not identify gene transcripts from SFBs and flagellin was undetectable in cecal contents from both SFB-monocolonized (formerly germ-free) WT and RAG1−/− mice (which lack antibodies entirely). The inventors observed that flagella harvested from pure cultures of the following species (*Roseburia intestinalis, Roseburia inulinovorans, Clostridium scindens, Clostridium ramosum, Clostridium bartlettii, Providencia stuartii, E. coli*) stimulate TLR5-reporter cell assays to the same degree as flagellin from *Salmonella enterica* serovar *Typhimurium*.

Flagellin is highly immunogenic and TLR5 is required for proper T cell responses against flagellin (Letran et al., *Eur. J. Immunol.* 41:29 (2011)), and furthermore, reduced anti-flagellin IgA levels have been noted in the serum of TLR5-deficient human hosts (Gewirtz et al., *Am. J. Physiol. Gastrointest. Liver Physiol.* 290:G1157 (2006)). The inventors assessed the levels of total and flagellin-specific IgA and IgG in the TLR5−/− gut. The inventors observed significantly lower levels of anti-flagellin IgA and IgG in the ceca of TLR5−/− compared to WT mice, despite higher total antibodies (FIGS. 1C, D). Anti-flagellin IgA levels were also low in MyD88−/− mice, whereas levels in DSS-treated WT mice were normal (FIG. 1D). These results show that loss of TLR5 signaling leads to reduced anti-flagellin IgA production in the gut regardless of inflammation. The inventors observed that antibodies from the WT mouse gut recognize flagella obtained from pure cultures of the following species: *Roseburia intestinalis, Roseburia inulinovorans, Clostridium scindens, Clostridium ramosum, Clostridium bartlettii, Providencia stuartii, E. coli, Salmonella enterica* serovar *Typhimurium*). These results show that the healthy WT mouse produces antibodies that can recognize flagellins from a wide diversity of bacteria.

The inventors next evaluated how the lack of antibodies against flagellin affected antibody-microbiota interactions in the gut. First, the inventors assessed the proportion of bacterial biomass coated by IgA in TLR5−/− and WT by sorting cecal bacteria into IgA-coated (IgA+) and uncoated (IgA−) pools using fluorescence-activated cell sorting (FACS). The proportion of IgA+ bacteria was similar for TLR5−/− and WT (21.7%±5.9 vs. 18.8%±4.2, n=4/group, n.s.). When incubated with a bacterial biomass previously unexposed to IgA (derived from RAG1−/− mice), IgA from both genotypes bound bacteria equivalently (55.7%±7.8% and 50.1%±7.8% of cells, respectively, n=4/group, n.s.). Together with the previous observations that IgA titers and bacterial biomass are higher in TLR5−/− mice (Vijay-Kumar et al., *Science* 328:228 (2010)), these results support the view that IgA induction functions as a stepwise response tailored to bacterial load (Hapfelmeier et al., *Science* 328: 1705 (2010)), and suggest that the absence of anti-flagellin IgA is compensated for with higher IgA overall titers.

Figure 2:
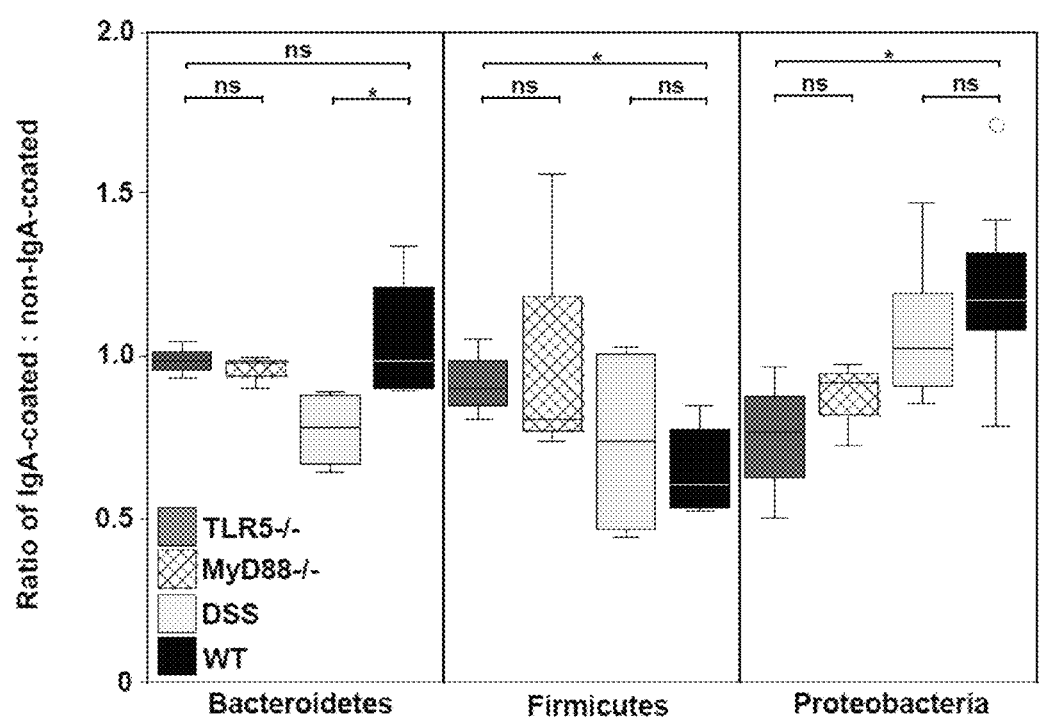
FIG. 2. Effect of TLR5 signaling on IgA coating of bacterial populations. (A) Box plots represent the ratio of IgA-coated to non-IgA-coated cecal bacteria for each genus within the specified phyla. N=4 mice/group; *P<0.05, two-tailed t-test; n.s., nonsignificant. An open circle represents an outlier. (B) The normalized abundance of 16S rRNA gene sequences from IgA+ bacterial cells are plotted against abundances for IgA− cells for the 25 most abundant genera. The 2 most abundant genera in each mouse phenotype are labeled. (C) Taxonomic classification of genus-level OTUs (97% ID) with significantly aberrant IgA-coating frequencies (based on Cook's distance, See Methods in Example 2).

To assess how loss of TLR5 signaling impacted the diversity of bacteria coated in IgA, the inventors profiled the bacterial diversity of IgA+ and IgA− cells from ceca of TLR5−/− and WT mice, as well as from MyD88−/− and DSS-treated mice, using pyrosequencing of 16S rRNA genes. If IgA binds widely to shared antigens, the coating frequency of bacterial genera is expected to be proportional to their abundance. This was the case for a majority of taxa, although a few outliers with high abundances were either more or less coated than expected (FIG. 2B-C). Patterns of bacterial coating were similar for TLR5−/− and MyD88−/− mice, and DSS-treated mice were similar to WT (with the exception of Bacteroidetes; FIG. 2A). Notably, TLR5−/− mice showed an enrichment of IgA+ Firmicutes and a depletion of IgA+ Proteobacteria. This pattern may indicate that a lack of anti-flagellin IgA is compensated with alternative antigen binding for Firmicutes, but not for Proteobacteria, which could be related to the inability of TLR5−/− hosts to manage Proteobacteria populations (Carvalho et al., *Cell Host Microbe* 16:139 (2012)).

Figure 3A:
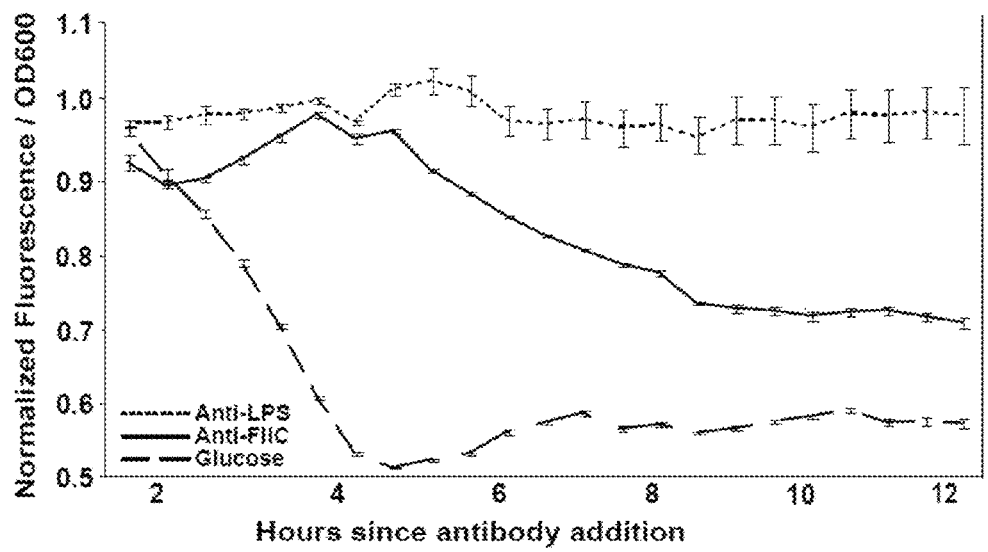
FIGS. 3A-3C. Anti-flagellin IgA reduces bacterial flagellin expression but does not affect bacterial fitness. (A) GFP FliC-reporter *E. coli* MG 1655 treated with antibodies. Glucose is a negative control as it downregulates flagella expression. Means ±s.e.'s. for ratios of GFP fluorescence: OD normalized to levels for untreated motile *E. coli* are plotted, n=3/group. (B) Flagellin load in ceca of gnotobiotic WT and RAG1−/− mice colonized with *E. coli* (Ec), Bacteroides thetaiotaomicron (Bt), and Bifidobacterium adolescentis (Ba). (C) CFU counts of bacteria cultured from the ceca. Bars are means ±s.e., *P<0.001; two-tailed t-test; n.s., non-significant.

To investigate the extent to which antibodies impacted flagella production directly, the inventors constructed a flagellin gene (FliC) reporter *E. coli* K12 strain. The addition of anti-LPS antibodies to the reporter culture reduced motility, likely reflecting steric hindrance, but had no effect on flagellin gene expression. In contrast, anti-flagellin IgA markedly reduced the expression of flagellin significantly within 2 hours of addition, and totally inhibited motility (FIG. 3A).

Figure 3B:
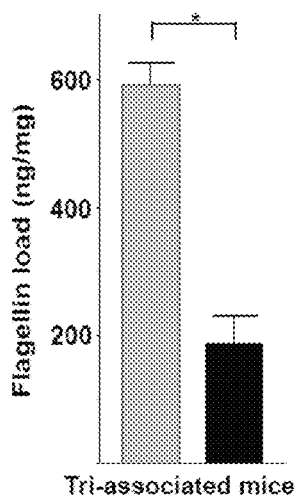
Figure 3C:
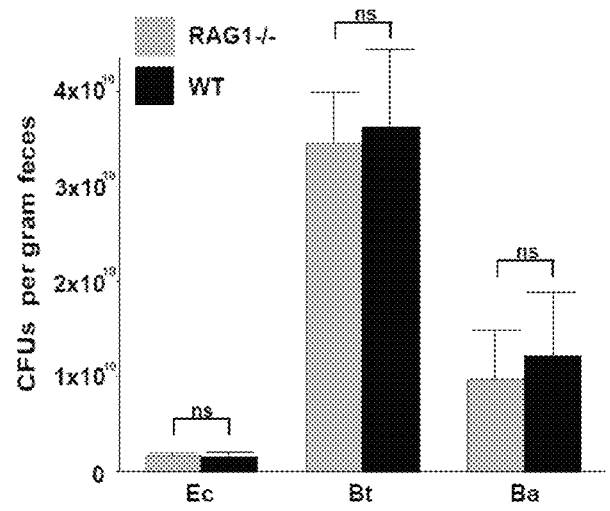
Figure 5:
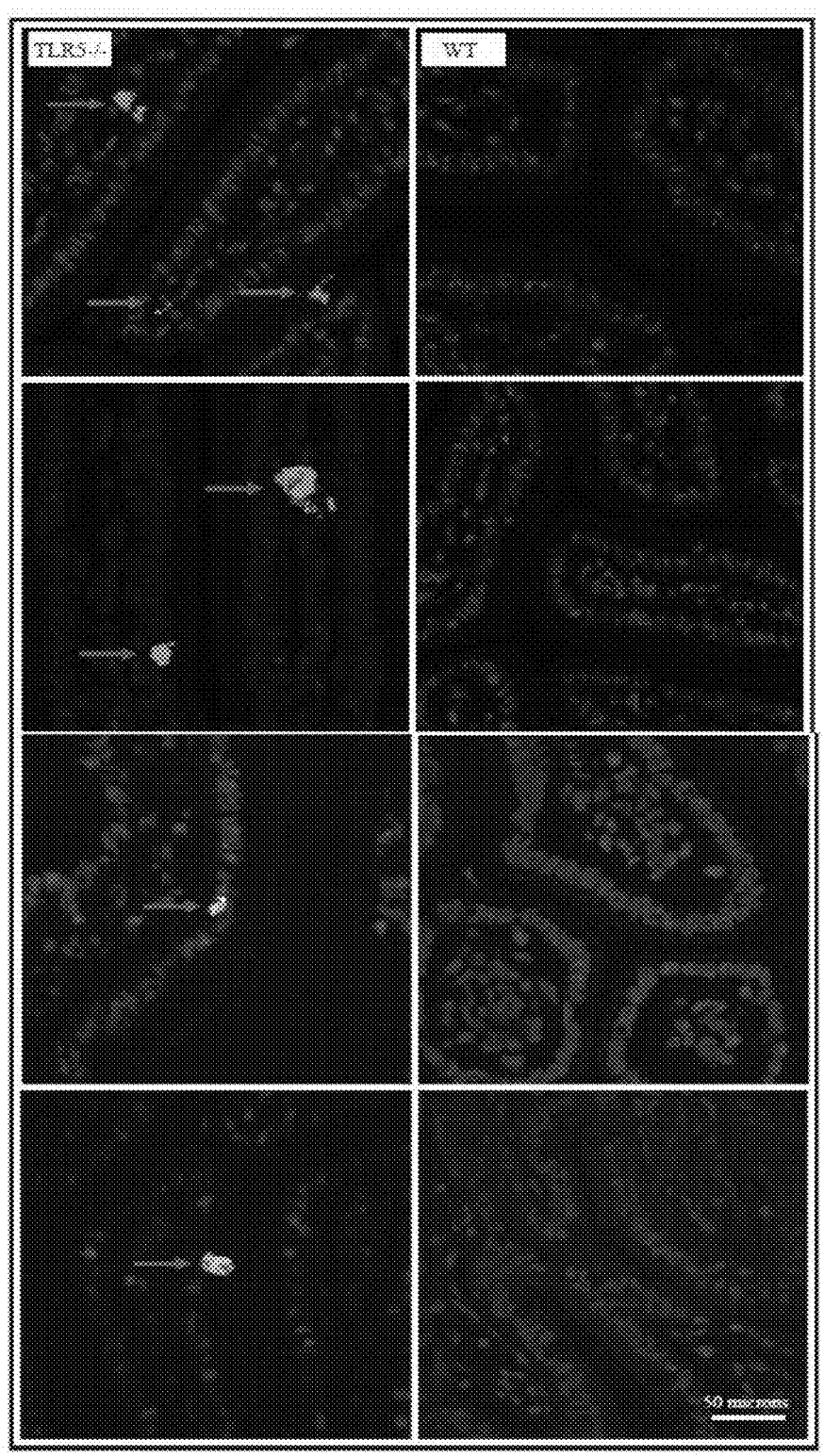
FIG. 5. γ-Proteobacteria and Firmicutes display increased penetrance of the small intestine of TLR5−/− mice. Each panel displays a fluorescent micrograph of a separate mouse small intestine section. TLR5−/− mouse sections are in the left column, WT on the right. BLUE: Nuclei of cells comprising host villi are stained with Hoechst 33342. GREEN: γ-Proteobacteria cells imaged by in-situ fluorescent hybridization (FISH) using fluorescently labeled oligonucleotides probes (specific 23S rRNA probe). ORANGE: FISH of Firmicutes cells. WHITE: The co-occurrence of γ-Proteobacteria and Firmicutes appears as white. Bacterial clusters are labeled with red arrows. The scale bar applies to all images.
Figure 6:
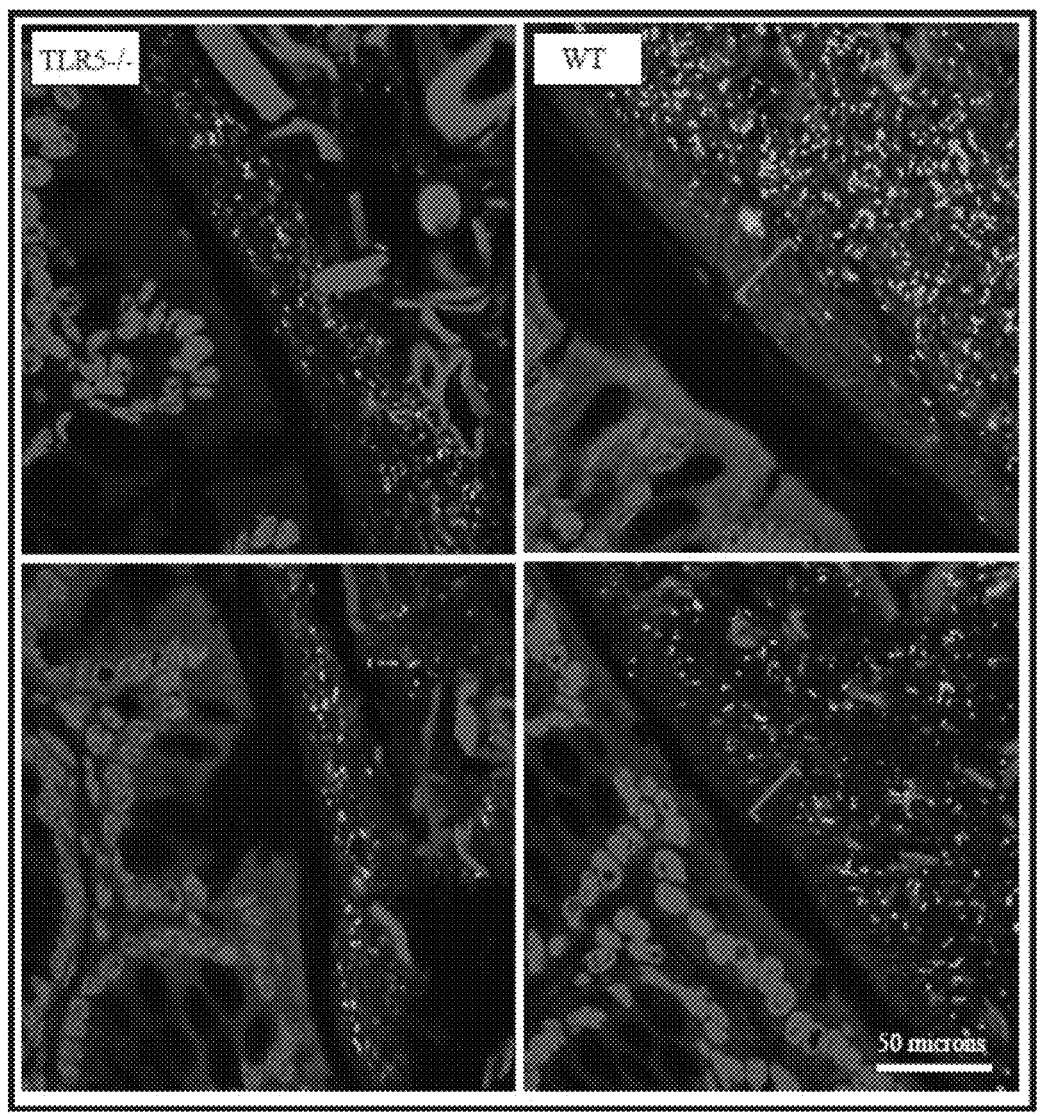
FIG. 6. The large intestine of TLR5−/− mice lacks mucosal integrity and displays increased bacterial penetrance. Each panel displays a fluorescent micrograph of a separate mouse large intestine section, with TLR5−/− mice (LEFT) and WT (RIGHT) shown. The images are positioned with host tissues on the left and the lumen on the right. BLUE: Nuclei of cells comprising host villi are stained with Hoechst 33342. GREEN: bacterial cells imaged by in-situ fluorescent hybridization using fluorescently labeled oligonucleotides probes (EUB338). Food particles in the lumen display autofluorescence and may fluoresce blue due to DNA content. Red brackets annotate the bacterially sparse inner mucus layer of WT mice that is absent in TLR5−/− mice. The scale bar applies to all images.
Figure 7:
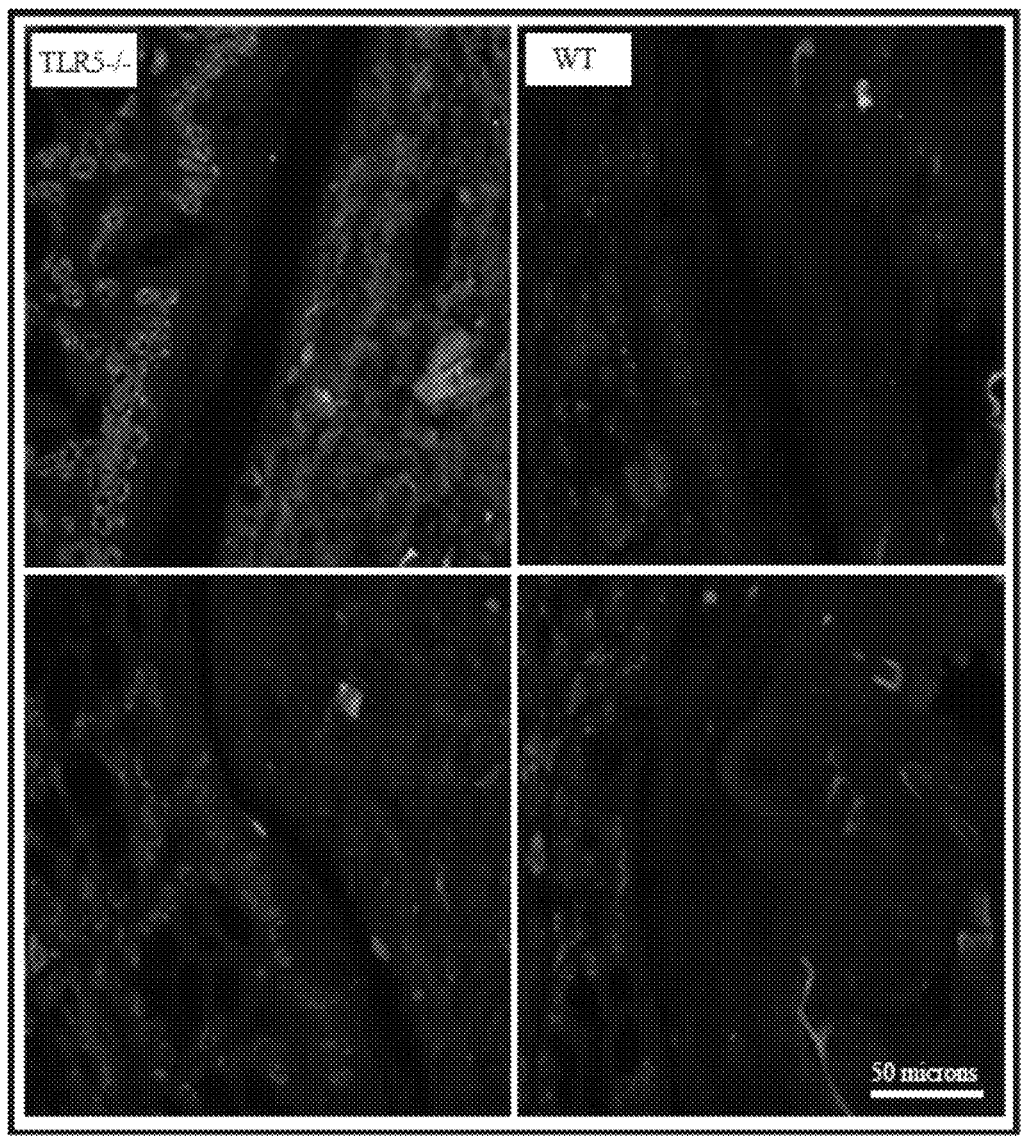
FIG. 7. Increased secretory IgA is apparent in the large intestine of TLR5−/− mice. Each panel displays a fluorescent micrograph of a separate mouse large intestine section, LEFT: TLR5−/− mice, RIGHT WT. The images are positioned with host tissues on the left and the lumen on the right. BLUE: Nuclei of host villi cells stained with Hoechst 33342. GREEN: IgA tagged with a fluorescent antibody. Food particles in the lumen display autofluorescence and may fluoresce blue due to DNA content. The scale bar applies to all images.
Figure 8:
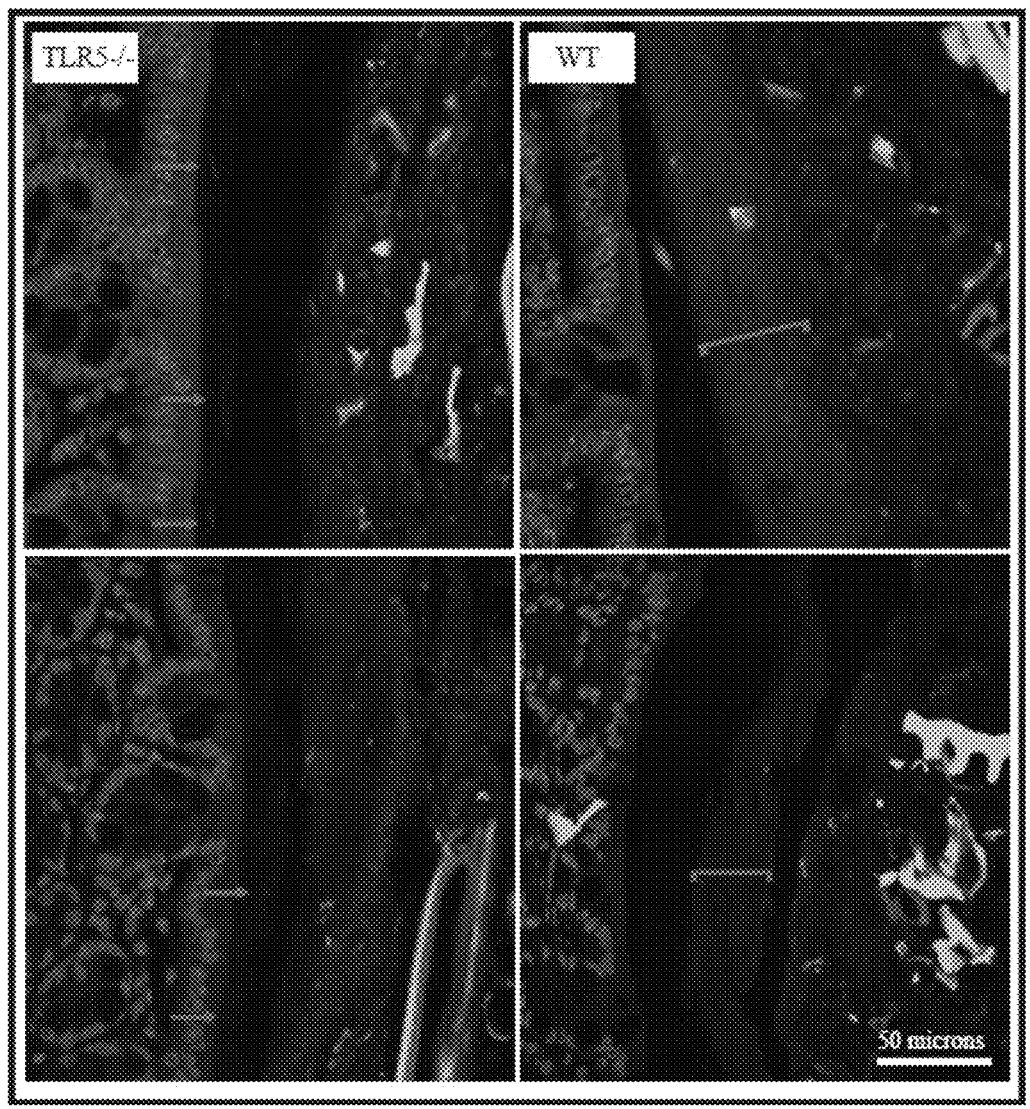
FIG. 8. Flagellated bacteria are more abundant in the large intestine of TLR5−/− mice and penetrate further into the mucus such that they directly contact the epithelium. Each panel displays a fluorescent micrograph of a separate mouse large intestine section, LEFT: TLR5−/− mice, RIGHT WT. The images are positioned with host tissues on the left and the lumen on the right. BLUE: Nuclei of host villi cells stained with Hoechst 33342. GREEN: flagellin tagged with a fluorescent antibody. Food particles in the lumen display autofluorescence and may fluoresce blue due to DNA content. Red arrows indicate bacteria in association with the epithelium. Red brackets indicate the bacterially sparse inner mucus layer of WT mice. The scale bar applies to all images.

To test if IgA-quenching of motility could affect the competitive balance of the microbiota, the inventors used a simplified gnotobiotic system to reliably quantify the entire population of flagellated bacteria. Germ-free RAG1−/− and WT mice were colonized with the motile *E. coli* strain MG1655 and non-motile *Bifidobacterium adolescentis* strain FST-1 and non-motile *Bacteroides thetaiotaomicron* strain VPI-5482. Flagellin levels in the RAG1−/− mice were significantly higher than in WT mice despite equivalent population levels of *E. coli* (FIGS. 3B,C). These results suggest that immune pressure drives down the expression of flagellin in the gut without impacting bacterial fitness.

Excessive flagellin and reduced anti-flagellin IgA in the gut could explain why TLR5−/− mice, and mice lacking components of adaptive immunity (i.e., SCID and RAG1−/− mice), are prone to developing inflammation (Keilbaugh et al., *Gut* 54:623 (2005)). The inventors hypothesized that elevated flagellin might promote inflammation by activating the NLRC4 inflammasome (Miao et al., *Semin. Immunopathol.* 29:275 (2007); Carvalho et al., *Mucosal Immunol.* 5:288 (2012)). Consistent with this notion, the inventors found that the loss of NLRC4 protected TLR5−/− mice against development of metabolic syndrome (FIGS. 4A,B). Together these findings indicate that TLR5−/− hosts are deficient in anti-flagellin IgA, resulting in the production of excess flagella in the gut, which triggers inflammation via NLRC4.

The inventors measured levels of anti-flagellin IgA and flagellin in fecal samples obtained from 43 healthy adults (62.5±1.3 years old) with a range of body mass indices (BMI). Consistent with the observations in mice, the inventors found that anti-flagellin IgA levels were inversely proportional to flagellin in human feces ($R^2$=0.39, FIG. 4C). Interestingly, fecal samples from normal-weight subjects (18.5≤BMI≤25) contained significantly higher levels of anti-flagellin IgA and lower flagellin compared to obese subjects (BMI≥30), while overweight subjects (25≤BMI≤30) had intermediate values (FIG. 4D). Thus, it is believed that that excessive gut flagellin, which can result from impaired adaptive immune response to flagellin, could be a risk factor for metabolic syndrome in humans.

Figure 9:
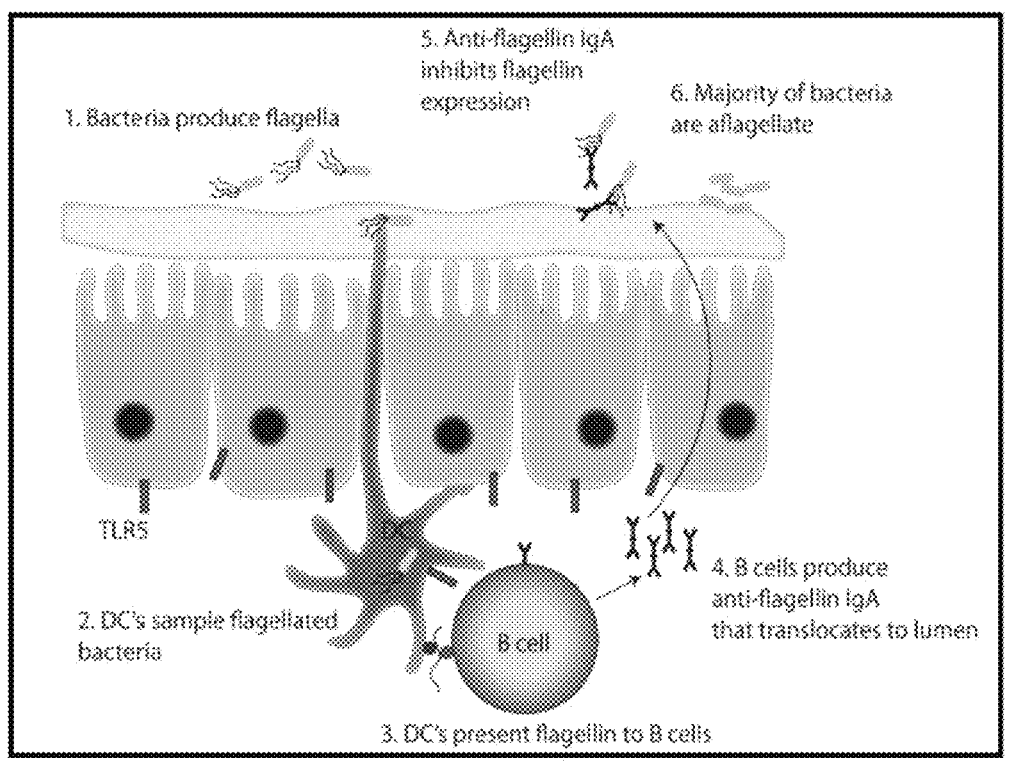
FIG. 9. Cartoon of a conceptual model for immune quenching of bacterial motility. Model of gut homeostasis showing the repression of flagellin production in the healthy gut. Blue cells are endocytes, the mucus layer is shown in grey. 1 and 2: flagellated bacteria can penetrate into the mucus above the epithelium, and are sampled by dendritic cells (DC's, purple); 3, 4: DC's present flagellin to B cells (red), which produce anti-flagellin IgA; 5, 6: Anti-flagellin IgA inhibits flagella production. Note that TLR5 (shown as a red rectangle) is expressed basolaterally on the endocytes and also on the DC.

The inventors believe that antibody quenching of bacterial motility is a fundamental component of homeostasis in the mammalian gut, and that bacteria are active participants in this process (FIG. 9). IgA is generally thought to bind bacterial cells to host mucus, inhibiting their penetration through the mucosal barrier and staving off damaging inflammatory responses (Salim et al., *Inflamm. Bowel. Dis.* 17:362 (2011); Turner, *Nat. Rev. Immunol.* 9:799 (2009)). The results above suggest an additional, specific role of IgA: down-regulation of motility genes (i.e., motility quenching), which would further reduce the microbiota's ability to penetrate mucus. While a few studies have shown that specific bacterial species can evade IgA coating by halting production of antigen to specific IgAs (Lonnermark et al., *Inst. J. Med. Microbiol.* 302:53 (2012); Friman et al., *Infect. Immun.* 64:2794 (1996); Peterson et al., *Cell Host Microbe* 2:328 (2007)), this evasive behavior can be extended to the microbiome as a whole. This explains how, although a majority of the healthy human gut's 100 trillion bacteria are capable of motility (Turnbaugh et al., *Nature* 444:1027 (2006); Kurokawa et al., *DNA Res.* 14:169 (2007)), flagellin is only a small component of a healthy gut proteome (Verberkmoes et al., *ISME J.* 3:179 (2009)). The inventors believe that normal gut homeostasis requires a balance between motility and immune pressure. The inability to control commensal motility in the gut can be a factor predisposing a host to inflammation, and is believed to represent a novel target for therapeutic intervention for the treatment and prevention of metabolic disease.

EXAMPLE 2

This Example describes materials and methods used in performing the experiments described in Example 1.

Human subjects: All work involving human subjects was approved by the Cornell University IRB (Protocol ID 1108002388). Human subjects were female Caucasian participants in the TwinsUK registry of King's College London (Spector et al., *Twin Res. Hum. Genet.* 9:899 (2006)). Subjects collected and refrigerated stool at their homes in 15 mL conical tubes 1-2 days prior to delivering the samples during their annual clinical visit at King's College London. Stool was stored at −80° C. prior to processing. Body Mass Indices were obtained as previously described (Spector et al., *Twin Res. Hum. Genet.* 9:899 (2006)). The inventors measured total IgA in 131 samples that were randomly selected from a total of 582 samples collected. Based on the initial analysis of total IgA, the inventors measured anti-flagellin IgA and flagellin levels in the 28 samples that presented the highest and lowest IgA values (14 of each chosen out of the 131 samples measured, irrespective of their BMIs). After observing a relationship between BMI and flagellin load, an additional 15 samples were then selected that presented the highest (8 samples) and lowest (7 samples) BMIs (irrespective of the total IgA content) from the set of 582 to balance out the samples in the 3 BMI categories.

Animal experiments: All mice used in this study were C57BL/6 strain. All mice used in FACS, metagenomics, and metatranscriptomics were maintained at Emory University. Mice used in flagellin and antibody quantification were either (1) obtained from the Jackson Laboratories and maintained at Cornell University, (2) derived as previously described and housed at Emory University, or (3) housed at the University of Nebraska, Lincoln. All gnotobiotic mice were developed and maintained at University of Nebraska, Lincoln. All animal experiments were approved by the local IACUCs. Additional TLR5−/− ceca used to quantify flagellin load across facilities were obtained from University of Pittsburgh and University of California Davis (provided by David Hackam and Stephen McSorley, respectively). MyD88−/−, NLRC4−/−, and TLR5/NLRC4 DKO mice were maintained at Emory University. For DSS treatment, C57BL/6 WT mice were administered 2.5% DSS (MBL Biomedicals) in drinking water for 7 days immediately preceding sample collection.

Measurement of antibodies via ELISA: the inventors measured total IgA, total IgG, flagellin-specific IgA, and flagellin-specific IgG in fecal and cecal samples by ELISA as previously described (Sitaraman et al., *Am. J. Physiol. Gastrointest. Liver Physiol.* 288:G403 (2005); Newton et al., *Science* 244:70 (1989)). Briefly, ELISA plates (Santa Cruz Biotechnology, Inc., Santa Cruz, Calif.) were coated overnight at 4° with 1 μg/ml of purified flagellin from *Salmonella typhimurium* strain 14028 (Enzo Life Sciences, Inc., Farmingdale, N.Y.) or left uncoated for total antibody quantification. Fecal and cecal samples were prepared by diluting to 0.25 mg/ml in PBS and homogenizing for 10 seconds using a Mini-Beadbeater-24 (BioSpec, Bartlesville, Okla.) without the addition of beads. The detection antibodies used were goat anti-mouse IgA or anti-mouse IgG-HRP (Sigma, St. Louis, Mo., USA) and TMB was used as a colorimetric reagent (Sigma, St. Louis, Mo., USA). Reactions were stopped with 0.18M $H_2SO_4$ before reading at 450 nm with a Synergy H1 plate reader (Biotek, Winooski, Vt.). Results are representative for 2 repeats of the experiment, each of which included 1 technical replicate per sample.

Sorting of IgA-coated bacteria: Four age/gender matched 8-week old TLR5−/−, MyD88−/−, WT DSS-treated, and WT mice were sacrificed and their ceca were immediately removed and snap frozen in liquid $N_2$. Cecal contents were prepared for fluorescence-activated cell sorting (FACS) of IgA-coated bacteria as described (Van der Waaij et al., *Gut* 38:348 (1996)). Briefly, cecal contents of mice were suspended in 4.5 ml PBS, homogenized on a vortex mixer, and centrifuged at low speed (40g, 20 min) to separate larger cecal particles from bacteria. The resulting supernatant was separated and centrifuged at 8,000 g for 10 min to remove non-bound IgA. The bacterial pellet was then resuspended in 2 ml of PBS containing 1% weight/volume of BSA with and without FITC-labeled goat F(ab')$_2$ anti-mouse IgA (Sigma, St. Louis, Mo.) and incubated for 1 h. Suspensions were washed and resuspended in 2 ml of PBS with and without propidium iodide (PI, 100 mg/l). Samples were stored on ice in the dark and analyzed within 2 h.

The inventors performed flow cytometry with BD-Biosciences FACS Aria high speed flow cytometer/cell sorter utilizing a quartz cuvette for interrogation. Fluorophore excitation was performed by an Argon laser operating at 15 mW and 488 nm. Filter settings were 525 BP for FITC, 550 LP and 630 BP for measurement of PI. The inventors used standard ELITE software comprising the Immuno-4 program to determine the percentage of stained events. The discriminator was set on PI fluorescence as a specific probe for bacteria. The discriminator value was determined by a filtered, bacteria-free (0.22 μm Millipore, Molsheim, France) solution of PI/PBS (4 mg/l) and set at a level with minimal background noise. The inventors analyzed a portion of each sample incubated with PBS (background fluorescence) and a portion incubated with FITC-labeled goat F(ab')$_2$ anti-mouse IgA. Both measurements were performed with 10,000 events, at a flow rate of 1000-1500 events/sec. Percentages of stained bacteria were determined with Immuno-4 software (Coulter). Sorting experiments were performed with gates on FSC>1000 and on FSC<1000 in combination with gates on side scatter or PI. Furthermore, a sorting experiment was performed with a FSC-FITC fluorescence gate to isolate a strongly IgA-coated bacterial population. A minimum of 500,000 cells of each category (IgA-bound and non-bound) were collected.

16S rRNA gene sequencing and analysis: Cells were collected the sorted by FACS (see above) and bulk DNA was extracted using the PowerWater DNA isolation kit as described by the manufacturer (MoBio Laboratories Ltd, Carlsbad, Calif.) using a Mini-Beadbeater-24 (BioSpec, Bartlesville, Okla.) set on high for 2 min. Bacterial 16S rRNA genes were amplified from each sample using the 27F and 338R primers for the V1-V2 hypervariable region of the 16S rRNA gene (Koren et al., *Proc. Natl. Acad. Sci. USA* 108 *Supp* 1:4595 (2011)). Primers included unique error-correcting 12-base barcodes used to tag PCR products from different samples (Hamady et al., *Nat. Methods* 5:235 (2008)). PCR reactions consisted of 2.5U Easy-A high-fidelity enzyme and 1× buffer (Stratagene, La Jolla, Calif.), 200 nM of each primer, 2-3 ng DNA template; reaction conditions consisted of an initial denaturing step for 2 min at 95° C., followed by 32 cycles of 40 s at 95° C., 30 s at 57° C. and 60 s at 72° C. Triplicate PCR reactions were performed for each sample, combined and then purified with Ampure magnetic purification beads (Agencourt, Danvers, Mass.). The clean PCR products were quantified using Quant-iT PicoGreen dsDNA assay (Invitrogen, Carlsbad, Calif.). The pooled products were sequenced at the Core Laboratories Center at Cornell University using the Roche 454 FLX platform.

For quality filtering the inventors discarded sequences <200 bp or >1,000 bp, and ones containing >0 primer mismatches, uncorrectable barcodes, >0 ambiguous bases, or homopolymer runs in excess of 6 bases using the open source software package Quantitative Insights into Microbial Ecology (QIIME) (Caporaso et al., *Nat. Methods* 7:335 (2010)). The inventors checked sequences for chimeras (UCHIME) and assigned to operational taxonomic units (OTUs) using Otupipe (Edgar et al., *Bioinformatics* 27:2194 (2011)) with a 97% threshold of pairwise identity, and then classified them taxonomically using the Greengenes reference database (McDonald et al., *ISMS J.* 6:610 (2011)). The inventors rarified samples to 7,000 reads per sample, calculated the ratio of IgA+: IgA− for each OTU, and calculated Cook's distance in R to find OTUs with IgA coating ratios that diverged significantly from the mean (Ferrari et al., *Journal of Applied Statistics* 31:799 (2004)).

Metatranscriptomic analysis: Six age/gender matched 8 week old TLR5−/− mice and their WT littermates were sacrificed and their cecal contents were immediately placed in RNAlater solution (Qiagen) and frozen. To prepare the samples for extraction, the inventors thawed and briefly centrifuged the samples and pipetted off the supernatant containing the RNAlater solution. The inventors enriched for nonribosomal RNA using a modification of a technique previously described (Stewart et al., *ISME J.* 4:896 (2010)). The inventors divided cecal contents in half and extracted bulk RNA and bulk DNA in parallel using the Powersoil RNA Isolation kit and Powersoil DNA isolation kit, respectively, as described by the manufacturer (MoBio Laboratories Ltd, Carlsbad, Calif.). The inventors generated sample-specific ribonucleotide probes targeting bacterial 16S and 23S rRNA genes by PCR amplifying these gene sequences from bulk DNA using the universal primers 27F and 1492R for 16S and 189F and 2490R for 23S. The inventors separately converted 16S and 23S rRNA gene sequence amplicons to biotinylated antisense rRNA probes, which hybridized to complementary rRNA molecules in the total RNA sample. The inventors confirmed subtraction efficiency by observing the absence of 16S and 23S rRNA peaks from the total RNA profiles using a 2100 Bioanalyzer and the RNA 6000 Pico chip kit (Agilent, Santa Clara, Calif.). Next, the inventors converted rRNA-subtracted samples to double-stranded cDNA, amplified via in vitro transcription, and converted back to double-stranded cDNA, which the inventors used directly for pyrosequencing at the Core Laboratories Center at Cornell University using the Illumina HiSeq 2000 platform. The inventors used the LSU and SSU reference databases from SILVA to separate Illumina reads with >70% similarity to a database rRNA sequence. Using this approach, the inventors identified 40.2% of the reads as ribosomal and removed them from downstream analysis. The inventors uploaded the non-ribosomal reads to MG-RAST (Meyer et al., *Bmc Bioinformatics* 9:386 (2008)) with the default quality filtering. COG relative abundance data for protein-coding reads were summarized using MG-RAST (e-value<$10^{-5}$; ID>50%; length>20 aa). The inventors uploaded functional assignments to Cluster 3.0 and centered and normalized counts before hierarchical clustering using the uncentered correlation similarity metric. This output was converted to a heatmap using Java Treeview 1.1.4r3 (Saldanha, *Bioinformatics* 20:3246 (2004)). To assign taxonomy to sequences annotated as flagellin, the inventors used hierarchechal classification and the Subsystems database in MG-RAST to annotate function using default cutoff parameters. The inventors isolated reads with an annotation of flagellin and assigned taxonomy using BLASTX (Altschul et al., *J. Mol. Biol.* 215:403 (1990)) with default arguments. The inventors visualized the BLAST results using MEGAN version 3.2.1 (Huson et al., *Genome Res.* 17:377 (2007)).

Metagenomic analysis: Four age/gender matched 8-week old TLR5−/− mice and their WT littermates were sacrificed and their ceca were immediately removed and snap frozen. The inventors extracted bulk DNA as described above, and quantified the purified DNA using Quant-iT PicoGreen dsDNA assay (Invitrogen, Carlsbad, Calif.). The products were assigned unique Multiplex Identifiers (MIDs) and sequenced at the Core Laboratories Center at Cornell University on the Roche 454 FLX platform. An additional 4 mice of each genotype were similarly processed and sequencing was performed at the DNA Sequencing Lab (Columbia University Medical center) using the Illumina HiSeq 2000 platform. The inventors quality filtered sequence reads (trimmed ends at quality scores with code "B" or any ambiguous base) and uploaded to MG-RAST (Meyer et al., Bmc Bioinformatics 9:386 (2008)) with the default quality filtering and without identical read dereplication. Taxonomy assignments (LCA) and COG relative abundance data for protein-coding reads were summarized using MG-RAST (e-value<$10^{-5}$; ID>50%; length>20 aa).

Construction of a short-lived FliC-GFP promoter fusion in *E. coli*: To examine the effect of anti-flagellin antibodies on flagellin expression in vitro, the inventors created a fliC reporter in pJBA110, a multi-copy vector containing the gene for a short-lived Gfp (Andersen et al., *Appl. Environ. Microbiol* 64:2240 (1998)). Briefly, the fliC promoter region was PCR amplified with primer set fliC promoter F-KpnI (5'CAG GTA CCG CGG TAA ACG ACG ATT GC 3' (SEQ ID NO: 1)) and fliC promoter R-XbaI (5'GGT CTA GAG CCA GAA GAC AGA CGC TC 3' (SEQ ID NO: 2)). The fliC promoter region that was used in this study contains sequence upstream of the fliC transcriptional start site (fliCp; GenBank Accession number AE000285, bases 3109-3597), included in this was the specified promoter sequence, IHP binding site, and the $\sigma^{28}$ binding site (Kundu et al., *Journal of Bacteriology* 179:4264 (1997)).

The inventors cloned the fliCp PCR product into pGEM T-Easy to give pGEM T-Easy fliCp. pGEM T-Easy fliCp and pJBA110 were digested with XbaI and KpnI, the fragments were gel purified and ligated together. The inventors electroporated the ligation reaction into *E. coli* PHL628, and selected clones which contained pJBA fliCp on LB (low salt) Km and Amp. The correct construct was confirmed by PCR using combinations of primers specific for the promoter region, fliC promoter F-KpnI and the gfp; P(gfp)-upF, P(gfp) upR and P(gfp).

Monitoring flagellin expression of *E. coli* bioreporter: The inventors grew *E. coli* in minimal salts medium (MSM) containing 0.2% glucose (as an inhibitor of flagellin expression) and ampicillin (15 mg/L) at 37° C. to an OD600 of 0.8±0.2. The inventors then diluted the culture 1:100 in MSM containing either 0.2% glucose or 0.2% casamino acids. The inventors divided cultures into 100 µl aliquots in 96 well clear flat-bottom plates (Costar, Corning, N.Y.) and incubated at 37° C. with periodic shaking on a Synergy H1, multiple detection microplate reader (Biotek Instruments Inc., Winooski, Vt.). OD600 and fluorescence of the fliC promoter fusion (Abs/Em: 488/509 nm) were measured every 30 min over the course of 15 hrs. Antibodies were added after 2 h of growth at a concentration of (5 µg/ml) (Forbes et al., *Infect. Immun.* 76:4137 (2008)). The fluorescence values were normalized to growth. Results are representative for 3 repeats of the experiment, each of which included 1 technical replicate per sample.

Motility plates: The inventors confirmed downregulation of flagella using Luria-Bertani (LB) broth motility plates containing 0.3% agar. *E. coli* was grown in liquid LB at 37° C. to an OD600 of 0.8±0.2. 5 µl of liquid culture were stab inoculated with or without the addition of antibody (0.1 mg/ml) into the center of each plate. Plates were incubated at 37° C. for 14 h and imaged immediately using a BioDoc-It Imaging System (UVP, Upland, Calif.). Results are representative for 2 repeats of the experiment.

Flagellin quantification: Flagellin was quantified using HEK-Blue-hTLR5 cells according to the manufacturer (Invivogen, San Diego, Calif.). Briefly, between 10-100 mg of either cecal or fecal material was suspended in PBS at a concentration of 25 mg/ml and homogenized for 10 seconds using a Mini-Beadbeater-24 without the addition of beads (BioSpec, Bartlesville, Okla.). The samples were then centrifuged at 8,000 g for 2 min, the resulting supernatants were subjected to two 10-fold serial dilutions, and 20 µl of each dilution was applied to 180 µl of mammalian cells. After 20-24 h of incubation, the inventors applied cell culture supernatant to HEK-Blue Detection medium (Invivogen, San Diego, Calif.) and measured alkaline phosphatase activity at 620 nm every 30 min for 3 h on a Synergy H1 multiple detection microplate reader (Biotek Instruments Inc., Winooski, Vt.). Results are representative for 1 repeat of the experiment and both experiments included 1 technical replicate per sample. The inventors used purified *Salmonella typhimurium* strain 14028 flagellin (Enzo Life Sciences, Inc., Farmingdale, N.Y.) to produce a standard curve. As a control for TLR5 specificity, the inventors included 1 additional replicate per sample, per plate, to which anti-hTLR5 neutralizing antibody (5 µg/ml) (Invivogen, San Diego, Calif.) was added. Alkaline phosphatase measurements in these wells represented nonspecific activity and were subtracted from the final quantification.

Tri-associated gnotobiotic mice: *E. coli* MG1655 was streaked on MacConkey (BD) agar and grown aerobically overnight at 37° C. *Bifidobacterium adolescentis* BD1 and *Bacteroides thetaiotaomicron* VPI-5482 (ATCC-29148) were grown anaerobically on Rogosa SL (BD) (96 h) and Bile Esculin agar (BD) (48 h), respectively, at 37° C. The inventors picked colonies from *E. coli*, *B. adolescentis*, and *B. thetaiotaomicron* and grew them in LB (BD) media, MRS (BD) with 5% L-cysteine, and TYG medium, respectively. *E. coli* was grown aerobically overnight (14 h) at 37° C., while the other two cultures were grown anaerobically for 48 h at 37° C. The inventors washed the cultures once with PBS and mixed in volumetrically equal proportions immediately before inoculating germ-free C57BL/6 WT and RAG1−/− mice by allowing them to drink the bacterial mixture and also by applying it on their fur. Colonized mice were maintained in sterile isolators.

The inventors quantified the three bacterial species by selective culture from fecal samples. The inventors serially diluted fresh fecal samples in sterile PBS (pH 7.0) and plated serial dilutions on Rogosa SL for *B. adolescentis*, Brain Heart Infusion (BD) with 10% sheep blood and 0.2 mg/mL gentamicin for *B. thetaiotaomicron*, and MacConkey for *E. coli*. Rogosa SL and Brain Heart Infusion plates incubated anaerobically at 37° C. for 96 h and 48 h, respectively, before enumeration. MacConkey agar plates incubated aerobically at 37° C. for 24 h before enumeration.

The inventors also analyzed the bacterial communities of the tri-associated gnotobiotic mice by denaturing gel gradient electrophoresis (DGGE). DNA was extracted from gnotobiotic fecal pellets as described previously (Davis et al., *Int. J. Food Microbiol.* 144:285 (2010)), but with five phenol-chloroform-isoamyl alcohol (25:24:1) extractions. DGGE was performed as described previously (Davis et al., *Int. J. Food Microbiol.* 144:285 (2010)) using a 20% to 55% urea and formamide gradient.

Estimation of insulin sensitivity: Age-matched TLR5−/− and TLR5/NLRC4 DKO mice were fasted for 5 h and baseline blood glucose levels were measured with an Accu-Check Advantage blood glucose meter (Roche) using blood collected from the tail vein. Mice were injected intraperitoneally with 1.0 U insulin/kg body weight (Eli Lilly Co, Indianapolis, Ind.). Blood glucose were then measured at 15, 30, 60, 90, and 120 min after injection.

Statistics: Statistical analysis and linear regression analysis were performed in Microsoft Excel 2011, StatPlus 2009, R version 2.11.1, and IBM SPSS Statistics. Statistical tests were 1-way ANOVA, unpaired student 't'-test, or generalized mixed linear model, as indicated. Significance level of $p<0.05$ unless otherwise indicated.

What is claimed is:

1. A method of measuring the level of flagellin comprising:
   obtaining a gastrointestinal (GI) tract sample of an individual;
   detecting the level of flagellin in the sample, wherein the level of flagellin is detected by a cell-based assay that uses a mammalian cell expressing Toll-like receptor 5 (TLR5) or at least one receptor of the NLRC4 inflammasome; and
   measuring the level of the flagellin in the sample in comparison with a control level of flagellin in a GI tract sample of a normal healthy individual.

2. The method of claim 1, wherein the cell comprises a reporter gene whose expression is induced upon binding of the TLR5 or the at least one receptor of the NLRC4 inflammasome with the flagellin and leads to the generation of a detectable signal.

3. The method of claim 2, wherein the reporter gene is placed under the control of a promoter inducible upon the binding of the TLR5 or the at least one receptor of the NLRC4 inflammasome with the flagellin.

4. The method of claim 1, wherein an increased level of the flagellin in the GI tract sample of the individual compared to the control level is indicative of the presence of metabolic syndrome in the individual.

5. The method of claim 1, wherein said sample is selected from a fecal, intestinal, mucosal or oral sample.

6. The method of claim 1, wherein said cell is a mammalian fibroblast cell line.

7. The method of claim 3, wherein said promoter comprises an NF-κB response element, a capsase-1 response element, or an NLRC4 inflammasome response element.

8. The method of claim 2, wherein the reporter gene encodes an enzyme.

9. The method of claim 2, wherein the reporter gene encodes a fluorescent protein.

10. The method of claim 2, wherein the cell-based assay comprises the step of:
    contacting the cell with the GI sample to form a cell-sample mixture;
    incubating the cell-sample mixture to allow binding of the flagellin in the sample to the TLR5 or the at least one receptor of the NLRC4 inflammasome expressed by the cell, thereby inducing the expression of the reporter gene; and
    detecting the expression of the reporter gene.

* * * * *

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: synthetic oligonucleotide primer

```
<400> SEQUENCE: 1
caggtaccgc ggtaaacgac gattgc                                26

<210> SEQ ID NO 2
<211> LENGTH: 26
<212> TYPE: DNA
<213> ORGANISM: Artificial Sequence
<220> FEATURE:
<223> OTHER INFORMATION: synthetic oligonucleotide primer

<400> SEQUENCE: 2
ggtctagagc cagaagacag acgctc                                26
```